(12) United States Patent
Minter et al.

(10) Patent No.: US 8,518,645 B2
(45) Date of Patent: Aug. 27, 2013

(54) METHOD OF MUTAGENESIS

(75) Inventors: Ralph Raymond Minter, Cambridge (GB); Steven Godfrey Lane, Cambridge (GB); Robert George Edward Holgate, Cambridge (GB); Maria Anastasia Theresa Groves, Cambridge (GB)

(73) Assignee: MedImmune Limited, Cambridge (GB)

( * ) Notice: Subject to any disclaimer, the term of this patent is extended or adjusted under 35 U.S.C. 154(b) by 462 days.

(21) Appl. No.: 11/813,507

(22) PCT Filed: Jan. 9, 2006

(86) PCT No.: PCT/GB2006/000059
§ 371 (c)(1),
(2), (4) Date: Feb. 29, 2008

(87) PCT Pub. No.: WO2006/072801
PCT Pub. Date: Jul. 13, 2006

(65) Prior Publication Data
US 2008/0171365 A1     Jul. 17, 2008

Related U.S. Application Data

(60) Provisional application No. 60/642,729, filed on Jan. 10, 2005.

(30) Foreign Application Priority Data

Jan. 10, 2005   (GB) .................................. 0500417.1

(51) Int. Cl.
C12Q 1/68     (2006.01)
C12P 19/34    (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| | | | |
|---|---|---|---|
| 6,521,453 B1 * | 2/2003 | Crameri et al. | ............... 435/440 |
| 6,620,597 B1 | 9/2003 | Chen et al. | |
| 2002/0160389 A1 | 10/2002 | Rodriguez et al. | |
| 2004/0253729 A1 | 12/2004 | Bauer et al. | |
| 2005/0069539 A1 * | 3/2005 | Cohen et al. | ............... 424/141.1 |

FOREIGN PATENT DOCUMENTS

| EP | 1108783 | 6/2001 |
|---|---|---|
| WO | WO 89/12063 | 12/1989 |
| WO | WO 93/01288 | 1/1993 |
| WO | WO 93/13216 A1 | 7/1993 |
| WO | WO 00/58517 | 10/2000 |

OTHER PUBLICATIONS

Jurinke et al. Recovery of nucleic acids from immobilized biotin-streptavidin complexes using ammonium hydroxide and applications in MALDI-TOF mass spectrometry. Anal. Chem. (1997) 69:904-910.*
Pagratis, N.C. Rapid preparation of single stranded DNA from PCR products by streptavidin induced electrophoretic mobility shift. Nucleic Acids Res. (1996) vol. 24, No. 18, pp. 3645-3646.*
Fieschi et al. Polymerase chain reaction-based site-directed mutagensis using magnetic beads. Anal. Biochem. (1996) vol. 234, pp. 210-214.*
Chen et al, "Amplification of closed circular DNA in vitro," *Nucleic Acids Research*, 26(4): 1126-1127 (1998).
Xiao et al., "Research on the mechanism of gene multi-locus site-directed mutagenesis," *Progress in Nature Science*, 7(3):333-339, 1997.
Miyazaki et al., "Creating Random Mutagenesis Libraries Using Megaprimer PCR of Whole Plasmid,"*BioTechniques*, 33(5):1033-1038, 2002.
Wang et al., "Two-Stage PCR Protocol Allowing Introduction of Multiple Mutations, Deletions and Insertions Using QuikChange™ Site-Directed Mutagenesis," *BioTechniques*, 26:680-682, 1999.
Ling et al., "Approaches to DNA Mutagenesis: An Overview," *Analytical Biochemistry*, vol. 254, pp. 157-178, 1997.

* cited by examiner

*Primary Examiner* — Kenneth R. Horlick
*Assistant Examiner* — David Thomas
(74) *Attorney, Agent, or Firm* — Klarquist Sparkman, LLP

(57) ABSTRACT

The present invention relates to a method of mutagenesis for introducing mutations into a molecule and, in particular, to methods that may be applied to populations of molecules for the generation or screening of libraries involving the mutation of multiple molecules.

41 Claims, 6 Drawing Sheets

FIG. 2

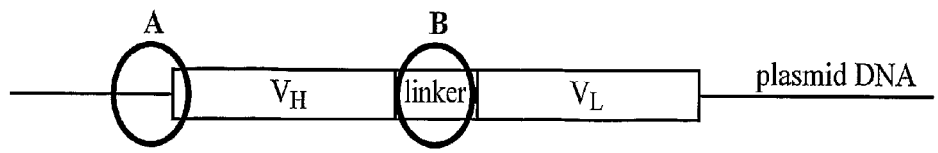

FIG. 2A

```
                                        V_H
                                    ┌───────→
                                    │
TGTTCCTTTCTATGCGGCCCAGCCGGCCATGGCCCAGGTCCAGCTGCAG

ACAAGGAAAGATACGCCGGGTCGGCCGGTACCGGGTCCAGGTCGACGTC

V  P  F  Y  A  A  Q  P  A  M  A  Q  V  Q  L  Q

Biotin-GCGGCCCAGCCGGCCATGG  bio-PAMA-IN (19-mer)
```

FIG. 2B

```
    V_H
←───────┐
        │
GTCTCGAGTGGAGGCGGCGGTTCAGGCGGAGGTGGCTCTGGCGGTGGCGGAAGT

CAGAGCTCACCTCCGCCGCCAAGTCCGCCTCCACCGAGACCGCCACCGCCTTCA

V  S  S  G  G  G  S  G  G  G  S  G  G  G  S

CCGCCTCCACCGAGACCGCCA H-link (21-mer)

H-link 5' to 3': ACCGCCAGAGCCACCTCCGCC
```

FIG. 3

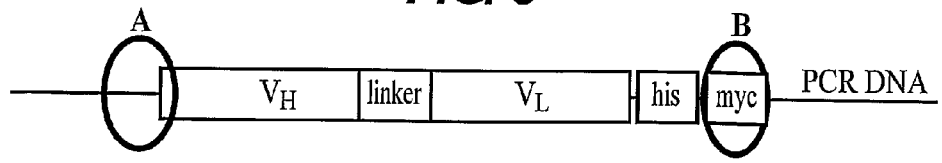

FIG. 3A

V<sub>H</sub> →

TGTTCCTTTCTATGCGGCCCAGCCGGCCATGGCCCAGGTCCAACTGCAG

ACAAGGAAAGATACGCCGGGTCGGCCGGTACCGGGTCCAGGTTGACGTC

V  P  F  Y  A  A  Q  P  A  M  A  Q  V  Q  L  Q

Biotin-GGCCGAGGTGCAGC bio-EVQ (14-mer)

Biotin-GGCCCAGGTGCAGC bio-QVQ (14-mer)

Biotin-GCGGCCCAGCCGGCCATGGCCGAGGTGCAGC bio-EVQ-LONG (31-mer)

Biotin-GCGGCCCAGCCGGCCATGGCCCAGGTGCAGC bio-QVQ-LONG (31-mer)

FIG. 3B

GAACAAAAACTCATCTCAGAAGAGGATCTGAAT

CTTGTTTTTGAGTAGAGTCTTCTCCTAGACTTA

E  Q  K  L  I  S  E  E  D  L  N

GAGTAGAGTCTTCTCCTAGACTTA MYC_RESTORE (24-mer)

MYC_RESTORE 5' to 3': ATTCAGATCCTCTTCTGAGATGAG

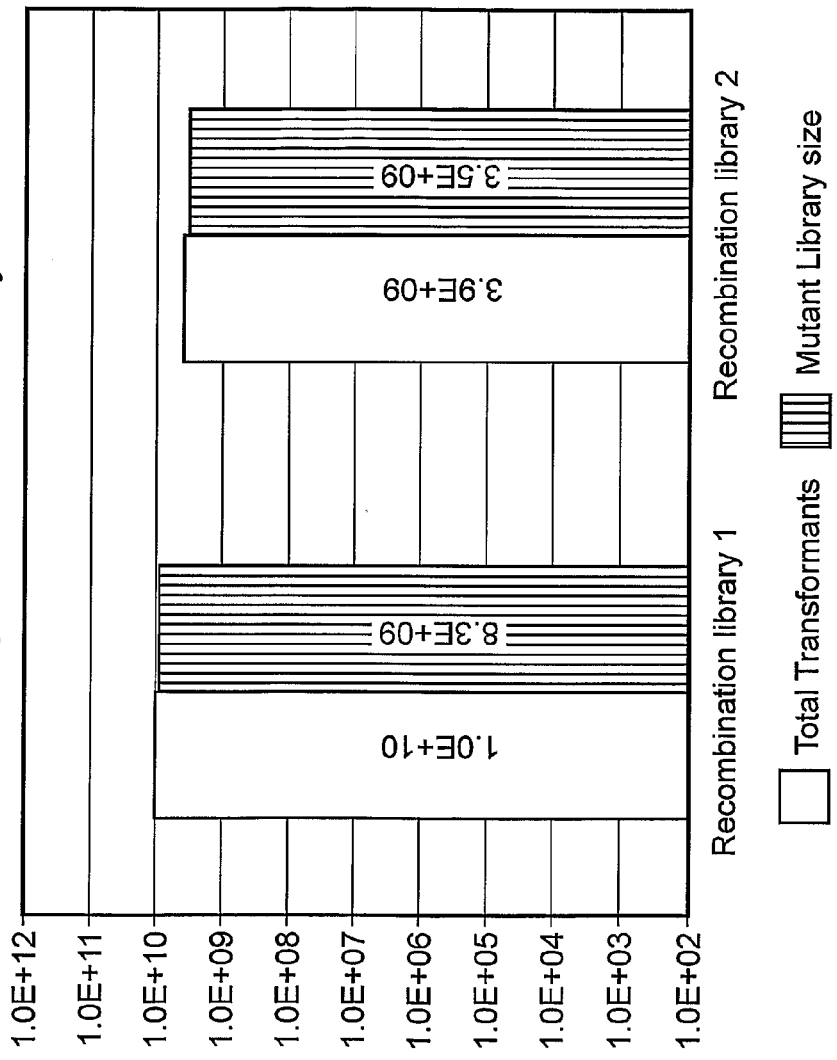

METHOD OF MUTAGENESIS

CROSS REFERENCE TO RELATED APPLICATIONS

This is the U.S. National Stage of International Application No. PCT/GB2006/000059, filed Jan. 9, 2006 (published in English under PCT Article 21(2)), which in turn claims the benefit of U.S. Provisional Application No. 60/642,729, filed Jan. 10, 2005 and of GB Application No. 0500417.1, filed Jan. 10, 2005. All of these applications are incorporated herein in their entirety.

The present invention relates to a method of producing mutagenised nucleic acid molecules. In particular, the present invention relates to a method in which the primer used in the mutagenesis reaction (the mutagenic primer) is, itself, synthesised from a template nucleic acid molecule. The output of the mutagenesis reaction is a mutagenised circular nucleic acid molecule which can be e.g., transformed into bacteria without the need for additional modification. In preferred embodiments, the method is applied to populations of molecules, for example in the creation of or screening of populations of molecules. The method may also be used in a combinatorial manner, in which multiple mutagenic primers are used to mutate multiple parent molecules.

One of the steps involved in molecular biological techniques is the introduction of nucleic acid into a vector. For example, a DNA fragment or population of DNA fragments may be digested and introduced by ligation into a vector. For example, a DNA fragment (or population of fragments) may be digested and removed from a first vector (e.g, a plasmid) into a second vector in a process known as sub-cloning. In this way, a first vector is digested with the same restriction enzymes as the second vector so as to produce complementary overhanging ends for ligation. The DNA fragment and the second vector are then ligated by virtue of their complementary overhanging ends and the result is a completed vector, containing the DNA fragment, that can replicate in a host cell (e.g in bacteria).

Hence large quantities of DNA may be produced for use in various molecular biological applications. Or, the vector into which the DNA has been introduced may have a particular purpose (e.g. may be an expression vector). Once introduced into such an expression vector, protein encoded by the restriction fragment may be expressed from the vector in the host cell. Once expressed, the resultant protein could be purified for its end use. Or, particularly where the method is used to incorporate a population of DNA fragments into an expression vector, the expressed protein may be used in a screen (e.g., by binding affinity to a target molecule).

Various methods of introducing mutations into DNA are also known. It is known from the work of Barik (Barik, *Methods in Molecular Biology Vol.* 192: *PCR Cloning Protocols*, 2$^{nd}$ edition p 189-196, Eds B-Y Chen and H. W Janes @ Humana Press Inc, Totowa, N.J.; Burke and Barik, *Methods in Molecular Biology Vo.* 226: *PCR Protocols*, 2$^{nd}$ Edition p 525-531, Eds J M S Bartless and D Stirling @ Humana Press Inc, Totowa, N.J.) to use a PCR-based approach to introduce mutations into linear DNA. According to these methods, so-called megaprimers have been used to introduce mutations into a linear template in a PCR reaction. However, such methods result in a linear, double-stranded DNA product that must itself be sub-cloned into an appropriate vector in order to produce a replicative form for e.g., scale up, or for protein expression.

Miyazaki proposed a method involving PCR of a whole plasmid (Miyazaki, *Methods in Molecular Biology. Directed Evolution Library Creation: Methods and Protocols*. Eds Arnold and Georgiou, Humana Press Inc. Totowa, N.J.; *BioTechniques* 33: 1033-1038). In this method, a double-stranded plasmid is used as the template in a PCR reaction and to which a double-stranded PCR product, containing the mutation to be introduced, is added for priming. However, the double-strandedness of the primer and template can cause the primer strands and the template strands to self-anneal rather than to cross-anneal and therefore a specific ratio of primer to template is used to minimise the self-annealing.

In addition to the problems of self-annealing that result from a double-stranded template, there are further problems when a double stranded template is used in a PCR reaction. In an exponential reaction the capacity for errors being introduced is high as an error introduced in one round is carried forward into each of the further rounds on an exponential basis. Furthermore where this PCR template is a large template such as a vector, e.g., a plasmid, then this further increases the likelihood of errors being introduced.

It is also known to use synthetic oligonucleotides to mutate DNA (Kunkel et al., (1985) *PNAS USA, Vol* 82, pp 488-492; Sidhu et al., *Phage Display for the Selection of Novel Binding Peptides*). However, there are limitations as to the length of the oligonucleotides that can be chemically synthesised. In addition, to program the synthesiser, the sequence must be known and inputted in advance into the synthesiser for its production.

There is therefore a need for alternative methods of mutagenesis. In particular, for methods that produce an output that can be directly transformed into bacteria, ready for downstream use, such as in expression screening (avoiding the need for additional digestion and ligation steps to introduce nucleic acid into an appropriate vector). There is also a need for fast, efficient mutagenesis methods and for methods that are amenable to scale-up, e.g., for use in the production of populations for screening or production of libraries.

The present invention, in one aspect, provides a method of introducing one or more mutations into a nucleic acid molecule, comprising: annealing a single-stranded form of a mutagenic primer to a parent molecule, said mutagenic primer having been synthesised from a template nucleic acid molecule and containing one or more mutations relative to said parent molecule; and synthesising a complementary strand from said mutagenic primer so as to produce a circular-form nucleic acid molecule containing said mutations.

In one aspect, the present invention provides a method of introducing one or more mutations into a nucleic acid molecule, comprising the following steps:
  (a) synthesising a mutagenic primer from a template nucleic acid molecule, wherein said mutagenic primer contains one or more mutations relative to a parent molecule;
  (b) separating a single-stranded form of said mutagenic primer;
  (c) annealing said single-stranded mutagenic primer to a single-stranded form of said parent molecule; and
  (d) synthesising a complementary strand from said mutagenic primer so as to produce a circular-form nucleic acid molecule containing said mutations.

Thus, the mutagenic primer is synthesised from a template nucleic acid molecule using a suitable enzyme, using methods known in the art. It is preferred that said mutagenic primer is synthesised using a polymerase chain reaction (PCR)-based method.

The template molecule and the parent molecule may be the same, or may contain the same sequence, which forms the basis of the synthesis of the mutagenic primer. Thus, in some embodiments, the sequence of the template for the mutagenic primer synthesis is the same as that found in the parent molecule. In these embodiments, the mutations may be introduced by virtue of the introduction of errors during the synthesis of the mutagenic primer from the template molecule, e.g., by means of an error-prone polymerase. Thus, in some embodiments, the mutagenic primer is synthesised by a synthesis method in which errors are introduced when synthesising a second strand from a first strand, preferably by error-prone PCR (suitable methods are known to the person of skill in the art, e.g, *Molecular Cloning: a Laboratory Manual: $2^{nd}$ edition*, Sambrook et al., 1989 *Cold Spring Harbour Laboratory Press*). Various kits are available in the art for carrying out error-prone PCR, such as Diversify (BDBiosciences 63070). In another approach, the template molecule may be transformed into an *E. coli* strain (suitable strains are available in the art, e.g., XL1-RED (Stratagene)) which introduces errors into the DNA sequence. Other methods for introducing errors into the mutagenic primer when produced from the template will be known to the person of skill in the art.

The template and the parent molecule may be different molecules, i.e., may contain regions in which there is a difference in sequence between the parent molecule and the template molecule respectively. Thus, when the mutagenic primer is synthesised from the template, it contains mutations in comparison with the parent molecule (in this situation, a reaction which introduces errors, e.g., error-prone PCR, is not needed).

The person of skill in the art knows of suitable reagents and reaction conditions for the synthesis of the mutagenic primer from the template (see, for example, *Molecular Cloning: a Laboratory Manual: $2^{nd}$ edition*, Sambrook et al., 1989 Cold Spring Harbour Laboratory Press). Where the mutagenic primer is synthesised using the polymerase chain reaction, suitable primers are chosen by the person of skill in the art, having regard to the template being used. The primers used to produce the mutagenic primer are referred to herein as the initial primers. These initial primers comprise a forward and a reverse primer, which are generally based on the ends of the sequence to be amplified, i.e., at the ends of the sequence that will be the mutagenic primer. The initial primers are generally synthetic oligonucleotides, produced by any standard methods using an oligonucleotide synthesiser. These initial primers may be of any suitable length, to for example around 15 to 100 nucleotides in length, e.g., around 15 to 75 nucleotides in length, around 15 to 50 nucleotides in length, generally 18 to 25 nucleotides in length. The skilled person can choose or design suitable initial primers, depending on, e.g., the sequence of template molecule, the size of the resultant mutagenic primer and/or the application of the method.

A further advantage of the present invention arises from the fact that the mutagenic primer is synthesised from a template nucleic acid molecule, so that the sequence of the mutagenic primer can be unknown to the user. For example, where the mutagenic primer is produced by PCR using initial primers directed to a known part of the template, the region amplified by these initial primers may be unknown. Thus in some embodiments, the sequence of the mutagenic primer is unknown prior to said annealing. This has particular application where the method of the invention is applied to libraries (discussed further below), but is not limited thereto. There are many other applications where a particular sequence, in subcloning is unknown, but the boundaries of the vector in which it is contained are known (one example would be in "shotgun" cloning). The skilled person, can select suitable initial primers based on his knowledge of the parent molecule.

The molecule defined in step (b) is thus a single-stranded mutagenic primer that has been isolated from its complementary strand and the terms separated and isolated are used interchangeably with respect to the single-stranded mutagenic primer. It is preferred that this separation or isolation of the single-stranded mutagenic primer from its complementary strand is carried out using a separating medium (such as beads or a separating column) as described below. In this manner a binding moiety may be introduced in to one of the strands of the mutagenic primer when it is synthesised, thus allowing one of the strands of the mutagenic primer to be isolated from the other e.g., in a capture step as described below.

It is preferred that the single-stranded primer defined in step (b) is separated by use of a separating medium. For example, the step of synthesising the mutagenic primer may introduce a binding moiety in either the positive strand or negative strand of the mutagenic primer and the separation of the mutagenic primer into its positive and negative strands may then be carried out via said binding moiety binding to its binding partner on a separating medium. The separating medium may be any suitable solid phase medium, such as beads or a column (e.g., beads or column to which is attached the binding partner).

More particularly, the binding moiety may be introduced into the positive strand of the mutagenic primer (e.g., by using an initial forward primer in the mutagenesis reaction that incorporates a binding moiety) and the negative strand of the mutagenic primer may then be eluted after the positive stranded form binds to the separating medium. It is preferred that the binding moiety is biotin and said binding partner is streptavidin. Other suitable binding moieties and binding partners will be known to persons of skill in the art and include fluoroscein and digoxin, and antibodies (including fragments and derivatives) and antigens.

The skilled person is well aware of other binding moieties and binding partners that could be used. For example, in addition to streptavidin, other binding partners that bind to biotin are available such as avidin and neutravidin. The skilled person can select suitable binding moieties and binding partners to use in the capture step involved in strand separation. In addition biotin and/or streptavidin analogues may be used (see e.g., J Mol Biol (1994) September 30: 242 (4):559-65)). Biotin and streptavidin are most preferred.

For example a particular antigenic moiety could be incorporated into one of the strands of the mutagenic primer during its synthesis, in a similar manner as that described for the biotin example mentioned above. Then one strand could be separated from the other using a column containing antibodies to the antigen.

Another approach is to use a separating system that contains proteins that bind to specific DNA sequences. For example it is known in the art that HaeIII methylase binds to a specific 5' DNA sequence, another example of protein that binds to a specific DNA sequence is P2A. For a discussion of such an approach see, Bertschinger and Neri "Protein, Engineering, Design and Selection (2004), Volume 17, page 699.

The binding partner and binding moiety should be of sufficient affinity to withstand the treatments that is used for separation of the DNA strands. For strand separation high or low pH may be used. Where low pH is used this is preferably ≦pH 3, more preferably ≦pH 2, even more preferably ≦pH 1. Hydrochloric acid and citric acid are preferred acids. High pH is more preferred. Where high pH is used this is preferably ≧pH 11, more preferably ≧pH 12, even more preferably ≧pH 13. Preferred alkaline agents include sodium hydroxide, and other Group I hydroxides such as LiOH or KOH. Group II hydroxides apart from Be(OH)$_2$ and Ba(OH)$_2$ could also be used. It is most preferred that the strands are separated using sodium hydroxide (e.g., 0.1N NaOH, which has a pH of 13). Appropriate agents and conditions can be selected by the person skilled in the art. Most preferred is the use of biotin and streptavidin and/or their analogues and high pH strand separation treatment as defined above.

Chemical groups could also be used to chemically attach one of the strands to a support. For example it is possible for oligonucleotides to be synthesised so as to incorporate a particular chemical group such as an amine or a thiol group. Indeed such oligonucleotides can be purchased from suppliers. Where such oligonucleotides are used as one of the initial primers in the reaction of the invention then the relevant chemical group will be incorporated into the relevant strand of the resultant mutagenic primer. The separation of the strands can then be brought about by coupling of these chemical agents (that are now incorporated into the DNA strand) to amine-linking agents or thiol linking agents, by way of example, and suitable agents are available to the person of skill in the art.

After the single stranded form of the mutagenic primer has been generated as described above, it is then introduced to the parent molecule to carry out the annealing step (c). In this way, the single-stranded form of the mutagenic primer is then added to the parent molecule for use in the annealing reaction.

In step (c), the annealing of the mutagenic primer to the parent molecule can use any suitable conditions and reagents, depending on for example the size of the mutagenic primer. The selection of appropriate conditions is understood by the person of skill in the art. By way of example, a molar ratio of 3:1 mutagenic primer to template may be used. Suitable reaction conditions are incubation at 90° C. for 2 mins, 50° C. for 3 mins and 20° C. for 5 mins. The conditions can be varied if necessary by the person of skill in the art.

The circular-form nucleic acid molecule resulting from step (d) is also referred to herein as the "output of the mutagenesis reaction" (or, in short-form, as the "output"). Preferably, the output of the reaction is replicative, meaning that on transformation into a host cell it can replicate to produce copies of itself. This has the advantage that the output of the mutagenesis reaction can be directly transformed into a host cell (such as a host cell for the purpose of expression of protein from the nucleic acid) without the need for further manipulations, e.g., without needing to excise the relevant portion of the nucleic acid with restriction enzymes and ligate into a further plasmid.

Alternatively, or additionally, it is preferred that the output of the mutagenesis reaction is double-stranded, to allow for digestion with restriction enzymes.

It is most preferred that the circular-form molecule (output of the mutagenesis reaction) is covalently closed circular DNA, preferably double-stranded.

As noted, step (d) produces a circular reaction product from the parent molecule. Such a reaction involves the priming of complementary strand synthesis from the annealed mutagenic primer, such that resultant complementary strand contains the mutations from the mutagenic primer. In general, the reaction mixture will contain suitable amounts of the nucleotide bases, DNA polymerase, DNA ligase and an appropriate buffer (the examples give suitable amounts). This is incubated under appropriate conditions for second-strand synthesis to be complete. Such methods are known to the person of skill in the art. It is preferred that this reaction be of a non-amplification type (e.g., a non-PCR-type reaction) so that it does not involve successive cycles of amplification and it could therefore be described as a linear reaction (i.e., one complementary strand is produced per parent molecule single-strand). For example, in the method of the invention, the mutagenesis reaction on the single-stranded parent molecule produces a second single strand which is opposite in sense to the single-strand of the parent molecule. Thus, where the single stranded parent molecule is a positive strand, the second strand synthesised in the mutagenesis reaction will a negative strand.

By using a single-stranded template and a single-stranded primer in the mutagenesis reaction, problems associated with self-annealing are avoided. Moreover, the output of the mutagenesis reaction is double-stranded and as such transforms bacteria more efficiently than a single-stranded molecule. Therefore, when transformed into a bacterial host, the mutated double-stranded form will transform bacteria in preference to the single-stranded template (effectively a selection of the mutated form over the non-mutated template).

The method of the invention comprises the steps listed above (herein, the term comprise is used in the sense of include, i.e., allowing the presence of one or more further features, e.g., reaction steps). Thus the method of the invention may include further steps, including but not limited to those steps mentioned elsewhere herein. The method of the invention may, alternatively, consist of the steps listed above, or mentioned herein. The steps of the reaction may be combined into single reaction vessels, and it is not necessary for each step to be carried out in a separate vessel. For example, the step of annealing the mutagenic primer to the parent molecule and the step of synthesising a complementary strand may be carried out in one vessel.

Preferably, the single-stranded parent molecule is single-stranded circular DNA. For example, the single-stranded parent molecule may be single-stranded circular DNA that is extracted from phage particles.

Preferably in the method of the invention, prior to said annealing step (c), there is the separate step of adding the single-stranded parent molecule to the single-stranded primer. More preferably, the method further comprises the step of isolating said single-stranded parent molecule prior to step (c).

The order of the steps relating to the mutagenic primer and the parent molecule, respectively need not be consecutive. Thus, the single-stranded form of the mutagenic primer may be separated before the single-stranded form of the parent molecule is isolated. Or, the single-stranded form of the parent molecule may be isolated before the single-stranded form of the mutagenic primer is separated. Or, the separation of the single-stranded mutagenic primer and the isolation of the single-stranded parent molecule, respectively, may be carried out side-by-side, or simultaneously.

It is preferred that the method of the invention further comprises a size exclusion step performed on said single-stranded parent molecule prior to step (c). For example, the single-stranded parent molecule is passed through a porous resin, any small fragments are trapped in the resin whereas the larger parent molecule passes through. This step removes short linear fragments of DNA (thought to be degradation products that co-purify with the template). Removal of these fragments improves the mutagenesis efficiency by avoiding priming events from the short fragments that do not lead to mutagenesis.

The parent molecule will contain the necessary sequence elements for the downstream use of the output of the method. Suitable vectors, for use as the parent molecule, are available in the art or may be constructed by the skilled person, using conventional techniques. Such vectors comprise appropriate regulatory sequences, including promoter sequences, termination sequences, enhancer sequences, marker genes etc. The vectors may be of any suitable type, e.g., plasmid, phage, phagemid etc. For example, where the output of the method is to be used in protein expression (for example, for screening of the expressed product) then the parent molecule will contain the necessary sequences for protein expression in a host cell.

Suitable expression systems are well known in the art, and a variety of host cells may be used. These include, bacteria, yeast, insect and mammalian cells (e.g., HeLa, CHO, or BHK cells). Bacterial cells are preferred, most preferably *E. coli*. Suitable vectors for each of these hosts are available in the art, or may be constructed by routine methods. Viral expression systems may also be used, such as baculovirus systems or plant viral expression systems. Techniques for the manipulation of DNA are well known in the art (e.g., cloning, sequencing, expression and analysis etc). Further details of known methods can be found in. e.g., *Molecular Cloning: a laboratory manual: 2nd edition*, Sambrook et al., 1989. Cold Spring Harbor Laboratory Press; or *Current Protocols in Molecular Biology, second edition*, Ausubel et al eds. John Wiley & Sons, 1992.

Preferably, the method of the invention further comprises the step of transforming the mutagenised nucleic acid molecule into host cells. Transformation may be by any suitable method and these are known to the skilled person. Examples include the heat shock method. It is preferred that said transforming is performed using electroporation. The step of transforming the mutagenised product may be carried out directly after step (d), or there may be intermediate steps between step (d) and the transformation into a host cell. In a preferred embodiment discussed below, transformation into a host cell is used to preferentially select the mutated complementary strand over the non-mutated parental molecule.

The method of the invention may comprise a step carried out under conditions such that the complementary strand containing the mutations is preferentially selected. Such preferential selection of the complementary strand may result from the preferential digestion of the parent molecule, or from the preferential survival of the complementary strand in a host cell.

The parent molecule may contain modifications such that the complementary strand is preferentially selected. The method of the invention may further comprise the step of introducing said modifications. In preferred embodiments, the modifications in the parent molecule include the introduction of dU in place of dT. Where the method further comprises the step of introducing such mutations, it is understood that this includes embodiments in which the parent molecule contains such modifications initially and further modifications are introduced in this step and embodiments in which there are no modifications initially and any such modifications are introduced by this step.

The situation in which dU replaces dT may be explained as follows. The parent molecule is grown in an *E. coli* strain that supports the introduction of uracil, e.g, a dut⁻ ung⁻ strain such as CJ236 (Kunkel et al., (1985) *PNAS USA, Vol* 82, pp 488-492; Sidhu et al., *Phage Display for the Selection of Novel Binding Peptides, Methods in Enzymology* 2000, *Volume* 238, page 333-363). According to these protocols the parent molecule is multiplied in *E. coli* in phagemid form. Single-stranded uracil-containing DNA is extracted via standard methods (e.g., the Qiagen M13 Spin Prep Kit). Following the annealing of the mutagenic primer to the single-stranded uracil-containing DNA, the complementary strand is synthesised (dT is used in the synthesis reaction rather than dU). This results in a heteroduplex DNA molecule, in which one strand (the parent strand) is dU-containing and does not contain the desired mutations and the second strand (the complementary strand synthesised in step (d)) is dT-containing and contains the mutations. The resultant molecule is then transformed into an *E. coli* host that does not support the presence of uracil, e.g., a dut⁺ ung⁺ host such as JM101. Thus the complementary strand containing the mutation is replicated in preference to the parent strand not containing the mutations (the parent, dU containing strand, is hydrolysed by uracil-glycosylase in the dut⁺ ung⁺ host).

Other selection methods include the use of methylation. The parent molecule will be methylated in almost all strains of *E. coli*. In step (d), a complementary strand can be synthesised in vitro that is not methylated, resulting in a heteroduplex comprising a methylated parent strand that does not contain the mutations and a non-methylated complementary strand that does contain the mutations. The heteroduplex is then digested with the Dpn1 restriction enzyme, which cuts double-stranded DNA at the site 5'-Gm⁶ATC-3' and is specific for methylated or hemimethylated DNA. Thus the parent strand is digested and the complementary strand containing the mutations is not. Alternative enzymes, e.g., other than Dpn1 may be used.

As a further possibility for the selection method, a conditionally lethal gene may be used. One example is ccdB, also known as the "control of cell death" gene. This gene could be inserted into the parent molecule into the region that would be replaced following the mutagenesis reaction. The parent molecule would be prepared from an *E. coli* strain that is not susceptible to this gene. The mutagenesis reaction would then replace the ccdB gene with the gene of interest. Those unmutated parent molecules, which still express ccdB will cause their *E. coli* hosts to die. Thus, the mutated molecules resulting from the mutagenesis reaction are selected.

Other suitable systems and selective enzymes may be used provided that they involve the selective breakdown, of the parent strand of the heteroduplex. Examples include endonucleases and endoglycosylases.

Thus in preferred embodiments, the method involves the use of a single-stranded parent molecule comprising modification to the nucleotides (e.g., dU replaces dT). Synthesis of the complementary strand primed from the mutagenic primer produces a newly synthesised mutated strand which does not include such modifications (e.g., by using dTTP rather than dUTP in the synthesis reaction). The non-modified, newly synthesised, mutated strand is preferentially selected (e.g., by transforming the heteroduplex molecule into a host cell that supports the replication of the non-modified, newly synthesised, mutated strand only, or by digesting the parent strand with a selective enzyme).

In a preferred embodiment, the invention provides a method wherein said preferential selection is carried out by transforming said circular-form molecule from step (d) into a host cell that is selective for the complementary, non-modified, strand (the newly synthesised, non-modified, mutated strand).

Thus, in a preferred embodiment, the invention provides a method of introducing one or more mutations into a nucleic acid molecule comprising the following steps:
(a) synthesising (preferably by PCR) a mutagenic primer from a template nucleic acid molecule wherein said mutagenic primer contains one or more mutations relative to a parent molecule;
(b) separating a single stranded form of said mutagenic primer;

(c) annealing said single-stranded mutagenic primer to a single stranded form of said parent molecule, wherein said parent molecule contains one or more selectable modifications;

(d) synthesising a complementary strand of said mutagenic primer so as to produce a circular-form nucleic acid molecule that does not contain said modifications;

(e) undertaking a selection step such that the complementary strand is selected in preference to the parent molecule.

In preferred embodiments, the method of the invention may be applied to populations of molecules. Thus, a population of molecules may be mutated using the above method, or a population of sequences may be inserted into an appropriate vector for screening (e.g., expression screening).

For example, the method may be used for creating a library of molecules. In this way, multiple mutagenic primers can be used to mutate a suitable vector to produce a library of products. Combinatorial mutagenesis using multiple mutagenic primers and multiple parent molecules may also be used to produce a library with extensive permutations. For example, multiple parent molecules with a variation at a first position in that molecule may be used in the mutagenesis reaction, together with multiple mutagenic primers that introduce mutations at a second position, thus generating an extensive library as a result of the combination or permutation of the variations at the first and second positions. This is exemplified by example 1 and illustrated schematically in FIG. 6.

The method may also be used to facilitate the screening of a population of molecules. For example a population of mutagenic primers may be derived from a population of template molecules. This population may then be introduced into e.g., a common vector, such as an expression vector for screening. This is exemplified in example 2.

Thus, in preferred embodiments the method is applied to populations of molecules, e.g, in the screening of a population of molecules or in the sub-cloning of a population of molecules to create a library. Thus, there may be a plurality of mutagenic primer, template and/or parent molecules. Such populations may be at least 1000 molecules in size, more preferably at least $10^4$, more preferably at least $10^5$, more preferably at least $10^6$, more preferably at least $10^7$, more preferably at least $10^8$, more preferably at least $10^9$, more preferably at least $10^{10}$, more preferably at least $10^{11}$, more preferably at least $10^{12}$, more preferably at least $10^{13}$.

Advantages associated with the application of the method of the invention to populations, especially libraries, are based in part, on the fact that the mutagenic primer sequences do not need to be known at the start of the protocol. Knowledge of a short region or regions of commonality in the template molecules (e.g., a known sequence that abuts a region of variability, or a known sequence in a vector that contains the template molecule(s)) allows the design of the initial primers. These initial primers may therefore be used to amplify a whole population of molecules that have variable regions as well as the common regions to which the initial primers are directed. Likewise a population of molecules may be inserted into a common parent molecule (e.g, a vector) for screening, such as expression screening, provided that there is region of complementarity between the mutagenic primer and the parent molecule. This region of complementarity may be the same as, or partially the same as, the region to which the initial primers were directed in the template molecule.

Thus, in the method of the invention, there may be multiple templates, or multiple forms of the template. For example, the template may be a library of different molecules contained within a vector, e.g., a plasmid. Thus, multiple mutagenic primers produced from such a library can then be used to produce a number of circular-form mutagenised outputs, because each of the multiple mutagenic primers introduces different mutations into the parent molecule when the complementary strand is synthesised in step (d). Where these multiple outputs are transformed into a suitable host, e.g., a bacterial host, such as *E. coli*, each resultant colony contains the output resulting from one of the multiple mutagenic primers.

Where multiple different mutagenic primers are to be produced from a library, e.g., a plasmid library, then the initial primers used to sythesise the mutagenic primer are chosen so as to be complementary to a region of the vector, which is common to the library. Thus, the multiple templates may comprise a region of variability and a region that is in common between the multiple templates. For example, the region of variability may be a randomised region of nucleic acid which is adjacent to regions that are non-randomised. In another example, the region of variability may be produced via multiple inserts having been introduced into multiple molecules of the same base vector. The initial primers are therefore chosen to be complementary to a region in the template that lies outside the region of variability, e.g., complementary to all or part of the non-randomised region of the template, or to part of the base vector. In this way, multiple mutagenic primers may be produced in one synthesis reaction using the same initial primers.

Alternatively or additionally, there may be multiple parent molecules. Thus, in step (c) the mutagenic primer may be annealed to multiple different parent molecules. Where there are multiple mutagenic primers, as previously described, these may also be annealed to multiple parent molecules. Thus a combinatorial effect can result, in which multiple mutagenic primers are annealed to multiple parent molecules with the production of combinations of mutagenic primers and parent molecules.

Thus the method of the invention may include multiple parent molecules and/or multiple mutagenic primer molecules.

This has the advantage that it can be used for large repertoires of parent molecules and/or templates, e.g. to combine large repertoires of parent molecules and/or templates. Preferred repertoire sizes are at least 100 parent molecule and/or templates, more preferably at least 1000, even more preferably at least 2500.

Using the combinational approach large repertoires can be produced, e.g. after combination of the various parent molecules with the various mutagenic primers there may be at least 1000 resultant outputs, more preferably at least $10^4$, more preferably at least $10^5$, more preferably at least $10^6$, more preferably at least $10^7$, more preferably at least $10^8$, more preferably at least $10^9$, more preferably at least $10^{10}$ more preferably at least $10^{11}$, more preferably at least $10^{12}$, more preferably at least $10^{13}$.

The mutations that may be introduced by this method include substitutions, deletions and additions. The mutations may be in a plurality of nucleotides (but may also be only in a single nucleotide). For example, a plurality of substitutions may be made in the parent molecule by the mutagenic primer, or a number of nucleotides may be deleted, or added. Combinations of the different types of mutations are also possible. Thus, there may be a combination of substitutions and deletions, a combination of substitutions and additions, a combination of additions and deletions, or a combination of additions, deletions and substitutions.

There may also be multiple regions of mutations, e.g., two regions in which one or more nucleotides are substituted, separated by a region in which no change is made by the mutagenic primer (because in this interstitial region, there is complementarity between the mutagenic primer and the parent molecule).

Further possibilities include: multiple regions in which one or more nucleotides are substituted, separated by regions of complementarity; multiple regions in which one or more nucleotides are added, separated by regions of complementarity; multiple regions in which one or more nucleotides are deleted, separated by regions of complementarity. Combinations are also possible. Thus there may be: one or more regions in which nucleotides are substituted and one or more regions in which nucleotides are added, separated by regions of complementarity; one or more regions in which nucleotides are substituted and one or more regions in which nucleotides are deleted, separated by regions of complementarity; one or more regions in which nucleotides are deleted and one or more regions in which nucleotides are added, separated by regions of complementarity; and one or more regions in which nucleotides are substituted, one or more regions in which nucleotides are added, and one or more regions in which nucleotides are deleted, separated by regions of complementarity.

The nature and number of the mutations is determined by the number and nature of the mismatches, as between the parent molecule and the mutagenic primer. Thus, where there is an addition of a single nucleotide in the mutagenic primer compared with the parent molecule then a single nucleotide will be added by virtue of the mutagenesis reaction. Where there are dispersed regions of mismatch in the mutagenic primer compared with the parent molecule (e.g., dispersed regions of additions, deletions and substitutions as set out above), this will result dispersed regions of corresponding mutations as a result of the mutagenesis reaction. The mutagenic primers may replace stretches of nucleotides in the parent molecule. For example, the mutagenic primer may contain a region of say 70% complementarity to the parent molecule and in this way, after the mutagenesis reaction, this region in the parent molecule is replaced by the 70% complementary region from the mutagenic primer.

In order for the mutagenic primer to anneal, there must be a degree of complementarity between the mutagenic primer and the parent molecule. There would typically be minimum regions of complementarity at the ends of the mutagenic primer. Where the mutagenic primer has been produced by PCR and the initial primers (defined above) are complementary to the parent molecule, then these provide a minimum region of 18 to 25 base pairs complementarity at the ends of the mutagenic primer.

The degree of complementarity over the whole of the mutagenic primer is preferably at least 60%, more preferably at least 70% more preferably at least 80%, more preferably at least 90%, more preferably at least 95%, more preferably at least 97%, more preferably at least 98%, more preferably at least 99%. By way of examples, at least 97% complementarity corresponds to 20 mismatches in a mutagenic primer that is 830 nucleotides long (810 complementary). At least 60% complementarity corresponds to a mismatch region in the mutagenic primer that is 730 nucleotides long and is 70% identical to the parent molecule in a mutagenic primer that is 830 nucleotides long (the two ends either side of the "70% region" being perfectly complementary to the parent molecule). Non-limiting examples of the mutagenic primers are shown in the figures.

The mutagenic primer may be from 100 nucleotides to 4000 nucleotides in length, preferably 200 to 3000 nucleotides, more preferably 300 to 2000 nucleotides, more preferably 400 to 1500 nucleotides, more preferably 400 to 1000 nucleotides, even more preferably 400 to 850 nucleotides in length or 800 to 1500 nucleotides in length.

The size of the mutagenic primer may depend upon the size of the parent molecule. For example, where the parent molecule is 5.5 kb the mutagenic primer is preferably up to 1 kb. Thus, the mutagenic primer is preferably around 1/50 to 1/5 the size of the parent molecule, more preferably 1/25, more preferably 3/10 the size of the parent molecule, most preferably around 1/5 the size of the parent molecule in nucleotides length.

It is preferred that the molar ratio of mutagenic primer to parent molecule in step (c) is around 2:1 to 5:1, most preferably around 3:1.

Preferred applications of the method of the invention include in the screening or creation of libraries, in particular antibody libraries. For example, the parent molecule may be a vector for the expression of antibodies or antibody domains. Having introduced mutations into the parent molecule (for example by making the mutagenic primers from a template comprising a library of antibody domains), the resultant mutated parent molecules can be expressed in a suitable host and screened against an appropriate antigen (for further information, see Vaughan et al., (1996) *Nature Biotechnology*, Volume 14, pp 309 to 314; and Edwards et al., (2003). *J. Mol. Biol,* 334, pp 103-118). Other antibody-related examples include the sub-cloning of antibody domains into an immunoglobulin acceptor plasmid, e.g., an IgG acceptor plasmid (such as a pEU IgG expression vector see Persic et al (1997) *Gene* 187:9-18. The term antibody describes an immunoglobulin and includes natural and synthetic versions. The term encompasses polypeptides having an antibody binding domain, which is or is substantially homologous to, an antibody binding domain. Examples include, Fab ($V_L$, $V_H$, CL and CH1 domains), scFv ($V_H$ domain and $V_L$ domain linked by a linker such as (Gly-Gly-Gly-Gly-Ser)$_3$, e.g., Bird et al (1988), *Science,* 242, 423-426, Huston et al. (1988), *PNAS USA,* 85 pp 5879-5883 Fv ($V_L$ and $V_H$ domains of a single antibody), Fd ($V_H$ and CH1 domains); dAb (Holt et al (2003), *Trends in Biotech.* 21 pp 484-490) and diabodies (WO94/13804).

Thus in preferred embodiments, the parent molecule, template or mutagenic primer comprises sequence encoding an antibody variable domain. The antibody variable domain may be a $V_H$ or $V_L$ domain. Preferably, the parent molecule comprises an scFv.

Where an antibody or antibody domain is referred to herein in the context of nucleic acid such as vectors, it is understood to refer to the nucleic acid sequence encoding that antibody or domain.

The method may also be used to shuffle antibody domains to create antibody repertoires. Thus, the parent molecule may contain an antibody $V_H$ domain and the mutagenic primer molecule may contain an antibody $V_L$ domain, or the parent molecule may contain an antibody $V_L$ domain and the mutagenic primer molecule may contain an antibody $V_H$ domain. A library of antibody $V_H$ domains may be combined (shuffled) with a library of antibody $V_L$ domains, or vice versa. Thus one of the two libraries may be used as the template to form multiple mutagenic primers and the other library may be present as a library in multiple parent molecules.

Thus the invention provides a method in which the parent molecule contains an antibody $V_H$ domain and an antibody $V_L$ domain and the mutagenic primer molecule contains an antibody $V_L$ domain to mutate the $V_L$ domain of the parent molecule. The invention also provides a method in which the parent molecule contains an antibody $V_L$ domain and an antibody $V_H$ domain and the mutagenic primer molecule contains an antibody $V_H$ domain to mutate the antibody $V_H$ domain on the parent molecule. In this way, a library of antibody $V_H$ domains may be combined (shuffled) with a library of antibody $V_L$ domains, or vice versa.

It may be desired that only one of the $V_L$ and $V_H$ domains of the parent molecule is to be mutated, or it may be desirable that both the $V_L$ and $V_H$ domains of the parent molecule be mutated. Single domain systems are also envisaged, e.g., in which the constructs contain a $V_L$ domain (but no $V_H$ domain) and that $V_L$ domain is mutated by a $V_L$ mutagenic primer, or e.g. in which the construct contains a $V_H$ domain (but no $V_L$ domain) and that $V_H$ domain is mutated by a $V_H$ mutagenic primer. The invention provides for all of these possibilities.

Thus, the invention encompasses the situation in which both the $V_H$ and the $V_L$ domains on the parent molecule will be mutated by mutagenic primers containing each of these domains. Thus a $V_H$ mutagenic primer would mutate the $V_H$ domain on the parent molecule and a $V_L$ mutagenic primer would mutate the $V_L$ domain on the parent molecule. A single mutagenic primer containing both of these domains could also be used.

The invention therefore provides a method, wherein first and second mutagenic primers are used to mutate the parent molecule, the first mutagenic primer containing an antibody $V_H$ domain to mutate the $V_H$ domain on the parent molecule and the second mutagenic primer containing an antibody $V_L$ domain to mutate the $V_L$ domain on the parent molecule. The first and second mutagenic primers may be used in separate mutagenesis reactions steps, in which case the first and second mutagenic primers may take part in separate mutagenesis reactions in any order (i.e. the first mutagenic primer could be used in a mutagenesis reaction preceding or succeeding the mutagenesis reaction involving the second mutagenic primer). Another possibility is that said first and second mutagenic primers are used in the same mutagenesis reaction step.

The aspects described above in which the method of the invention is used to combine (or shuffle) libraries of $V_H$ with libraries of $V_L$ domains in the antibody context could be applied to other systems in which the shuffling of combinations of domains is desired, such as other molecules related to the immunoglobulins and to multi-domain proteins in general. Thus the invention provides a method of combining a library of first domains with a library of second domains, as described above for the antibody aspects (in which the first domain is the $V_H$ domain and the second domain is the $V_L$ domain, or vice versa).

In some preferred embodiments, the parent molecule comprises nucleic acid encoding an scFv.

The present invention also provides kits for carrying out the above-mentioned methods. For example, such a kit may comprise initial primers suitable for synthesising a single-stranded primer molecule from a template molecule, a single-stranded parent molecule and instructions for use. The parent molecule may be modified as described herein. Suitable reagents and buffers may also be included, such as those referred to herein. Further kit components as defined in any of the embodiments of the method of the invention may also be included.

As noted, the methods and kits of the invention have a number of applications, including the following. The methods can be used in sub-cloning, for example a region of nucleic acid can be generated by step (a) and introduced into an appropriate vector by the mutagenesis reaction, avoiding the need for digestion and ligation of the nucleic acid. For example, a target antigen could be cloned into an expression vector. The methods may be applied to the creation and screening of libraries as mentioned above. More specific utilities are outlined below.

The methods described herein can be used to convert single chain Fv (scFv) fragments ($V_H$ and $V_L$ domains linked as a single peptide, via a linker) into IgG molecules. Thus, the $V_H$ and $V_L$ domains may be introduced into IgG_$V_H$ and IgG_$V_L$ acceptor plasmids. Using initial primers that are so-called generic oligonucleotides, directed to non-variable parts of the vector that contains the scFv, or to the linker between the two domains (e.g., one initial primer that is directed to the sequence upstream or downstream of each of the domains and a second initial primer that is directed to the linker between the two domains). For example, if using the scFvs described in Vaughan et al, one of the initial primers could be directed to sequence upstream of the $V_H$ domain in pCantab6 and the other to the linker (i.e. directed to part of the sequence encoding (Gly-Gly-Gly-Gly-Ser)$_3$).

The methods of the invention can also be used to generate naïve libraries (i.e., libraries from non-immunised human donors). Currently these are generated by carrying out PCR of naïve antibody $V_H$ and $V_L$ regions from non-immunised human donors, followed by restriction digest and ligation into acceptor plasmids. Using the method of the invention, mutagenic primers may be separated from these PCR products derived from the non-immunised donors. Again, the use of the above-mentioned methods removes the need for restriction and ligation. Suitable primers may be based on sequences at each end of the heavy chain and each end of the light chain (see, for example, Vaughan et al., supra).

Aspects and embodiments of the invention will now be illustrated by way of examples and with reference to the following figures, in which:

LIST OF FIGURES

FIG. 1 shows the mutagenic primers for use in the method of the invention. In each case, the numbers are the approximate number of bases and the mismatch region is in grey. FIG. 1a shows mutagenic primer 1, used in Example 1 ($V_H$/$V_L$ recombination). FIG. 1b shows mutagenic primer 2a, used in Example 2 (Ribosome Display subcloning) for $V_H$CDR3 variants. FIG. 1c shows mutagenic primer 2b, used in Example 2 for $V_L$ CDR3 variants. FIG. 1d shows a mutagenic primer for producing $V_H$ or $V_L$ variants. The region in grey is about 70% identical to the template of Example 2. FIG. 1e shows mutagenic primers for cloning into an IgG acceptor plasmid. FIG. 1f shows mutagenic primers for cloning into $V_H$ and $V_L$ acceptor plasmids for the creation of naïve libraries.

FIG. 2 shows the position of the initial primers for the synthesis of the mutagenic primer for the use in the $V_H$/$V_L$ recombination embodiments (e.g, Example 1). A and B show the forward and reverse primers, respectively.

FIG. 3 shows the position of the initial primers for the synthesis of the mutagenic primer for the use in the ribosome display aspects (e.g., Example 2). A and B show the forward and reverse primers, respectively.

FIG. 4 shows results of the mutagenesis procedure of Example 1.

Figure 1A:
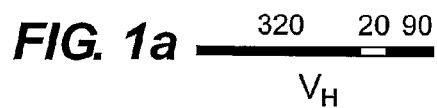
Figure 1B:
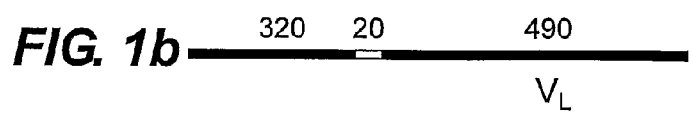
Figure 1C:
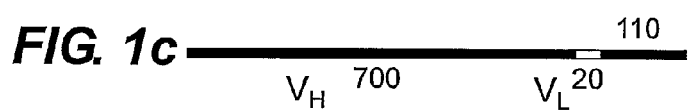
Figure 1D:
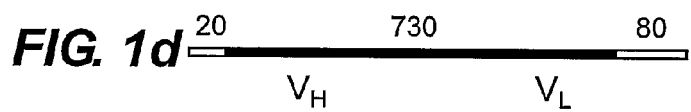
Figure 1E:
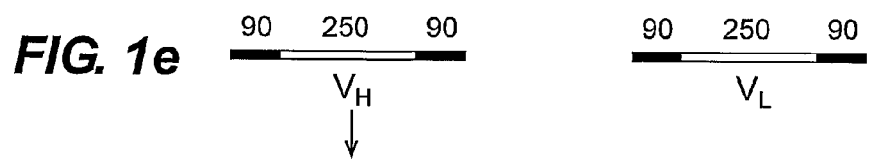
Figure 1F:
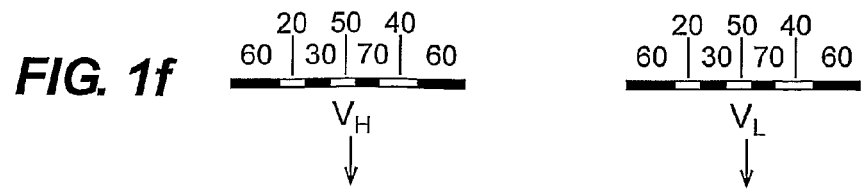
Figure 5:
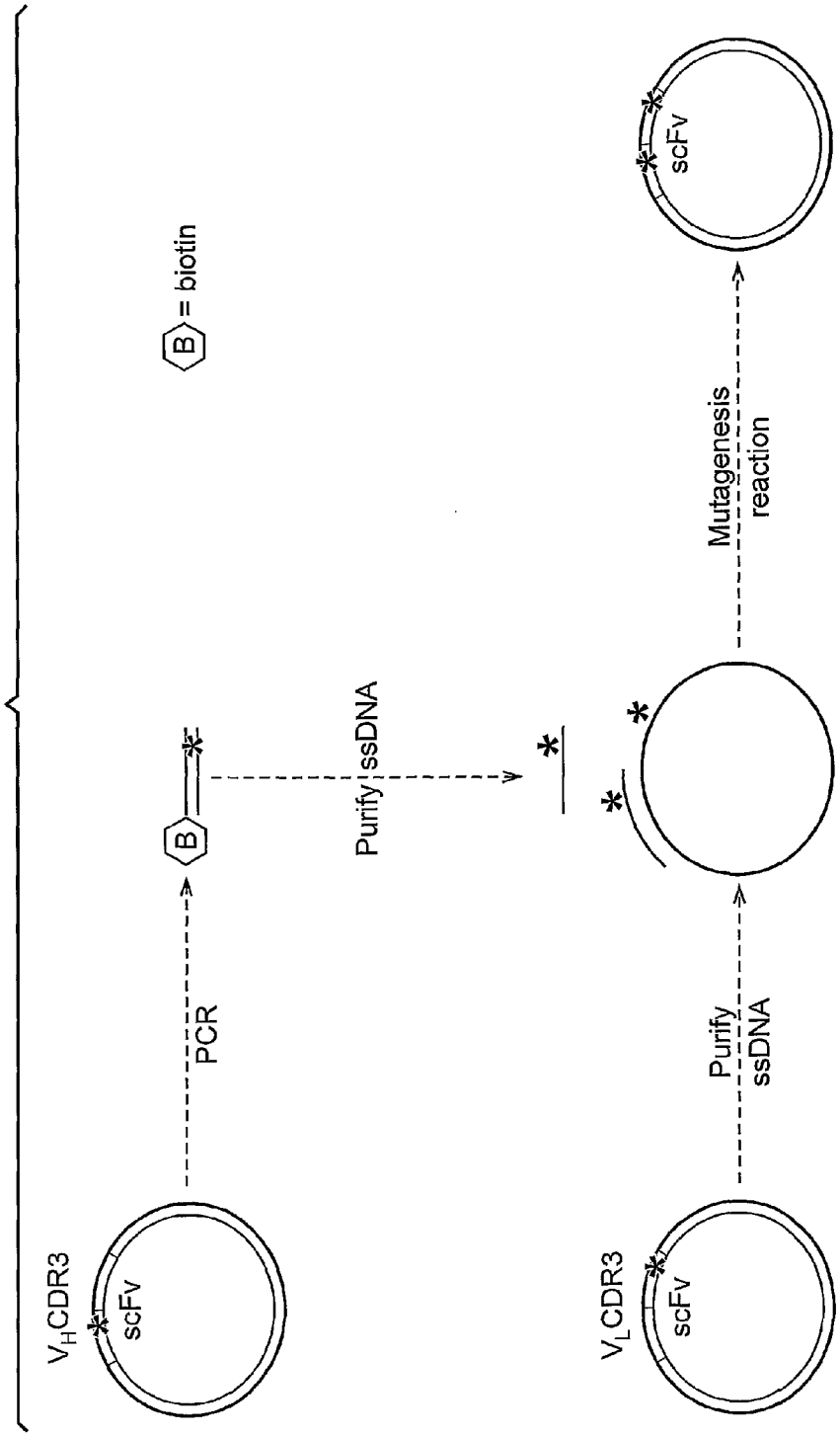

FIG. 5 is a schematic showing the mutagenesis procedure of the invention. In the schematic, the VHCDR3 from an scFv-containing plasmid containing a particular mutation in the VHCDR3 (shown by a star) is amplified by PCR and separated into single-stranded form by virtue of biotin being introduced by the primers in the PCR reaction. Single stranded DNA is purified from an scFV-containing plasmid, which contains a particular mutation in the VLCDR3 (also shown by a star). In the mutagenesis reaction between the single stranded PCR product containing the VHCDR3 mutation and the single-stranded plasmid containing the VLCDR3 mutation the two mutations become combined to produce an scFv-containing plasmid that contains both the mutations.

Figure 6:
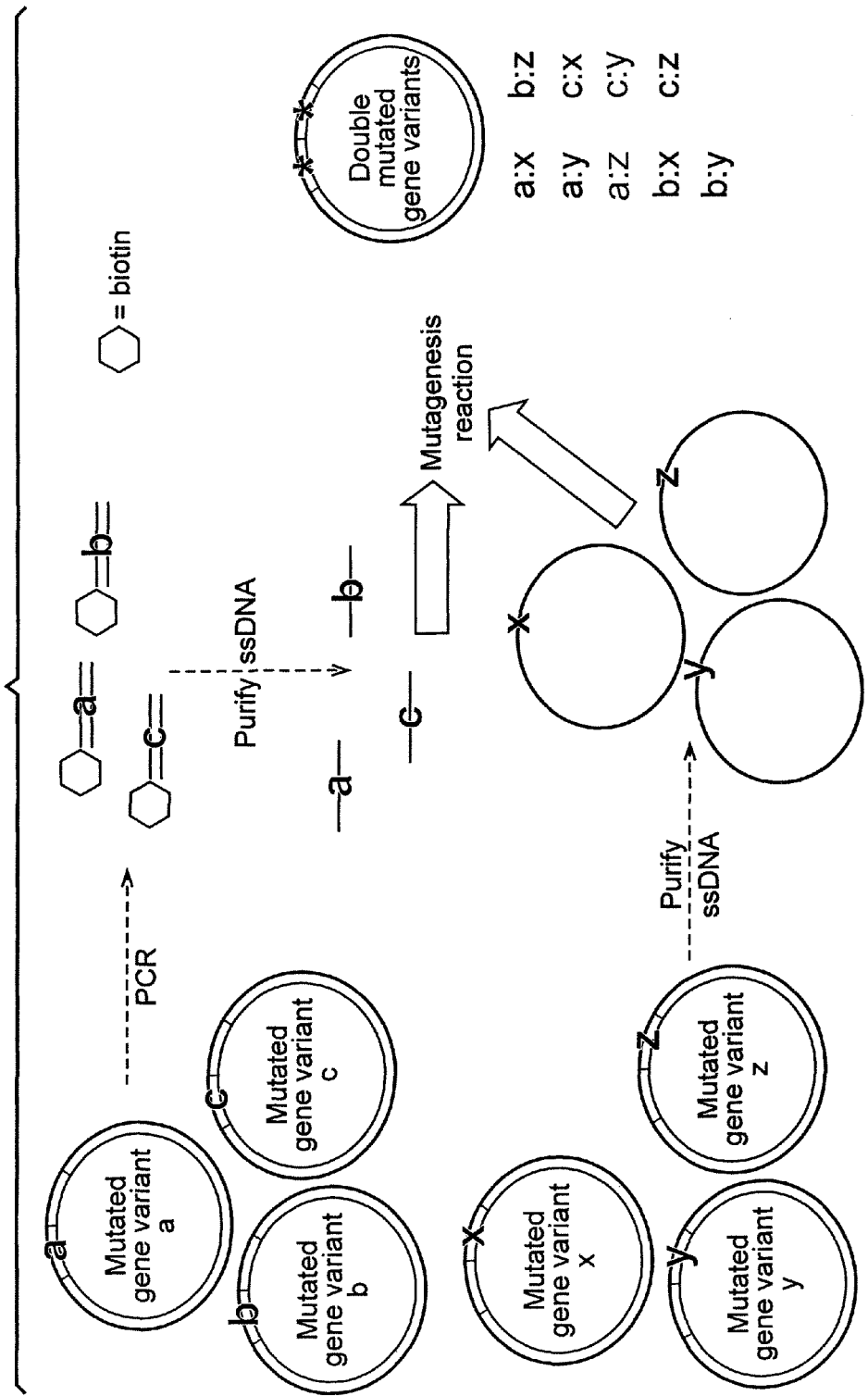

FIG. 6 shows a combinatorial embodiment of the invention. At the top of the figure are shown multiple template molecules that contain mutations a, b and c. The regions of these molecules containing the mutations are amplified by PCR and separated into multiple single-stranded mutagenesis primers using biotin. At the bottom of the figure is shown multiple parent molecules which contain mutations x, y and z. Single-stranded DNA is produced from these molecules, so as to result in multiple parent molecules each containing mutations x, y or z. In the mutagenesis reaction, the mutagenic primers containing mutations a, b and c are used to mutate the multiple parent molecules. This results in the combination of outputs shown in the right of the figure.

EXAMPLES

Example 1

Mutagenesis Method to Recombine Optimised $V_H$ and $V_L$ Regions

1. Overview of Method

The recombination of optimised $V_H$ and $V_L$ regions has been shown to lead to increases in potency during antibody affinity maturation in vitro (Osbourn et al, (1996), Immunotechnology, Vol 2, pp 181-196). In this example, the mutagenesis method of the invention is used to recombine one pool of variants in which the $V_H$CDR3 has been randomised with another pool of variants in which the $V_L$CDR3 has been randomised. Both pools of variants contain the same original antibody sequence, except for the short regions of randomisation in the $V_H$ and $V_L$ CDR3. Following randomisation, the $V_H$ and $V_L$ pools have each undergone two rounds of phage display selection for improved affinity. The $V_H$ and $V_L$ outputs of the round two selection, each containing an estimated $10^5$ to $10^6$ different variant sequences, form the starting point for the recombination method described in this example.

In the method of this example, the $V_H$ pool is amplified by PCR using the biotinylated PAMA-IN oligonucleotide at the 5' end and the H-LINK oligonucleotide at the 3' end (see FIG. 2). Following capture on streptavidin beads, the non-biotinylated strand is eluted and this forms the mutagenic primer.

The $V_L$ pool is prepared as single stranded plasmids, following rescue of bacteriophage particles from the dut– ung– E. coli strain CJ236. By bringing the $V_H$ encoding mutagenic primer together with the single stranded plasmids representing the $V_L$ pool, the recombination of $V_H$ and $V_L$ regions can occur.

2. Oligo Design

The dU-ss DNA template isolated from M13 is plus-strand so the mutagenic primer is complementary to the plus-strand (i.e. it is minus-strand). By biotinylating the forward primer, the minus strand can be eluted following capture on streptavidin. The oligonucleotides used are as follows (5' to 3'):—

```
Bio-PAMA-IN:    biotin-GCGGCCCAGCCGGCCATGG
H-LINK:         ACCGCCAGAGCCACCTCCGCC
```

3. Preparation of $V_L$ Outputs as dsPlasmid DNA

1. The glycerol stock of the $V_L$ repertoire in pCantab6 (Vaughan et al) was inoculated 100 ul into 50 ml 2×TYA in a small conical flask.
2. The culture was grown for 2 hours at 37° C. and 300 rpm.
3. Cells were pelleted by centrifugation in 50 ml Falcon tubes at 3200 rpm for 10 minutes.
4. Qiagen HiSpeed Plasmid Midi Kit protocol was carried out to isolate ds plasmid DNA in 1 ml water.
5. The concentration of DNA was checked by UV spectrometry or agarose gel.

4. du-ss DNA Template Preparation

The dsPlasmid DNA from part 3 was then used in the following protocol:

Reagents:

Plasmid Midiprep of $V_L$ repertoire in pCantab6 (Vaughan et al)

Chloramphenicol (CAM) at 10 mg/ml in ethanol and store at −20° C.

Uridine (Sigma U-6381) at 0.25 mg/ml in water and store at 4° C.

2×TYAG (+10 ug/ml CAM) plates: (TY is as described in Sambrook et al, supra plus 100 μg/ml ampicillin (A) and 2% glucose (G) chloramphenicol (CAM) is added at 20 μl stock to 80 μl ethanol and spread onto plate).

Preparation of $CaCl_2$ Competent CJ236

1. 5 ml of 2×TY media (plus 10 ug/ml CAM) is inoculated with a single colony of E. coli CJ236 cells (e.g., supplied by Biorad). Cells were grown overnight at 37° C. 300 rpm. CAM selects for F' episome in CJ236.
2. 500 ml of 2×TY was inoculated with 5 ml of the overnight culture and incubated with shaking at 37° C.
3. When the OD at 600 nm reached 0.9 the culture was harvested by centrifugation at 4° C. (5 min, 5,000 rpm). The supernatant was poured off and cell pellet drained. The cells were resuspended gently in 100 ml of ice cold 100 mM $MgCl_2$.
4. Cells were again harvested by centrifugation (centrifuge at 4° C.) and pellets were drained. Cells were gently resuspended in 20 ml of cold 100 mM $CaCl_2$ until a smooth suspension was obtained. 200 ml of cold 100 mM $CaCl_2$ was added and mixed. The cells were placed on ice for 30-90 mins.
5. The cells were harvested by centrifugation in a cold centrifuge and the pellets drained. Cells were resuspended in 20 ml of cold 85 mM $CaCl_2$ and 15% glycerol.
6. The cell suspension was aliquoted immediately (the aliquots can be frozen in dry ice/ethanol if need be).

Transformation of Template into CJ236

1. The CJ236 $CaCl_2$ competent cells from above were thawed on ice (and were kept on ice throughout the protocol).
2. 5 μl of pCantab6 plasmid containing the $V_L$ repertoire from section 3 was added to 100 μl of competent cells in a PCR tube.
3. The following programme was run on the PCR machine block:
   0.1° C. for 30 min
   42° C. for 45 s
   0.1° C. for 2 min
4. The cells were transferred 15 ml Falcon tube in 0.5 ml of 2×TY.
5. The cells were incubate at 37° C. for 45-60 min with shaking at 200 rpm.
6. 0.5 ml of cells were plated onto 2×TYAG (+10 ug/ml CAM) plates and the plates incubated o/n at 37° C.

Rescue of Phage from CJ236 and DNA Preparation

1. A lawn arising from step 6 above of CJ236 transformants was scraped into 1 ml 2×TY. 500 µl was inoculated into 50 ml 2×TYGAC (ie 2% glucose, 100 µg/ml AMP, 10 µg/ml CAM) and incubated at 37° C. and 300 rpm until $OD^{600}$=0.5 to 1.
2. The cell density was calculated from the OD reading ($OD^{600}$ of $1=5\times10^8$ cells/ml) and wild-type KO7 helper phage were added (Amersham Biosciences M13 KO7 Helper phage) to ensure a multiplicity of infection (MOI) of 10 phage: 1 cell (wt KO7 stock usually contains $10^{10}$ phage in 0.33 µl). The cells were then incubated at 37° C. (no shaking) for 10 minutes to allow infection.
3. 1 ml culture was transferred to 30 ml 2×TYAC supplemented with 25 ug/ml KAN (to select KO7) and 0.25 µg/ml uridine (to allow synthesis of uracil-containing template). This was incubated overnight at 37° C. 300 rpm.
4. Cells were centrifuged for 10 mins at 15000 rpm 2° C. in a SS-34 rotor. Supernatant was transferred to a fresh tube and ⅕ volume of PEG-NaCl was added (20% $PEG^{8000}$, 2.5M NaCl). This was incubated for 5 mins at room temperature and then centrifuged for 10 mins at 10000 rpm 2° C. in SS-34.
5. A small white phage pellet was produced. Supernatant was decanted and tube inverted on tissue to drain. The phage pellet was resuspended in 0.5 ml of PBS (the walls of the tube were rinsed to capture as many phage as possible). The phage were transferred to eppendorfs and centrifuged for 5 mins at 15000 rpm in a microfuge to pellet remaining insoluble matter. The supernatant was transferred to a new eppendorf.
6. The dU-ss DNA template was purified using a Qiagen Qiaprep Spin M13 kit, beginning with the addition of the Qiagen MP buffer (Sidhu et al, supra). The DNA was eluted in 100 µl 10 mM Tris-HCl, pH8.0 and examined on a 1% agarose gel The ss DNA preparation ran as a distinct band at 2.5 kb and was used in the mutagenesis reaction in section 6.
5. Preparation of ssDNA Mutagenic Primer from $V_H$ Repertoire The region representing the repertoire of different $V_H$ sequences was amplified from pCantab 6 by PCR using the oligonucleotides bio-PAMA-IN and H-LINK. Standard PCR conditions can be used on a dilution series of the midiprep template prepared in section 3.

| | |
|---|---|
| Abgene (2×) Mastermix | 25 µl |
| Template midiprep | 1 µl [neat, $10^{-1}$, $10^{-2}$, $10^{-3}$, $10^{-4}$, $10^{-5}$, $10^{-6}$, none] |
| Bio-PAMA-IN | 1 µl |
| H-LINK | 1 µl |
| Water | 22 µl |

5 µl of each PCR was run on a 1% agarose gel (this confirmed the product size, showed the yield etc).
1. A microMACS column (Miltenyi Biotec: 130-042-701) was placed in a magnetic rack.
2. 250 µl of 1× binding buffer (2× binding buffer: 10 mM Tris pH7.5, 2M NaCl, 1 mM EDTA, 0.1% Tween 20) was allowed to flow through.
3. 45 µl PCR reaction was mixed with 105 µl microMACS streptavidin beads (Miltenyi Biotec: 130-074-101) and 150 ul 2× binding buffer and incubated for two minutes.
4. DNA+ beads was applied to a microMACS column and allowed to flow through.
5. The column was washed with 2×1 ml 1× binding buffer.
6. DNA was eluted into eppendorf with 200 µl 0.1N NaOH (made fresh).
7. To the eluted DNA was added 20 µl sodium acetate pH5.2, 550 µl ethanol, 1 µl glycogen.
8. This was incubated at −70° C. for 30 minutes.
9. This was centrifuged at 13000 rpm for 10 minutes to pellet DNA. The supernatant was removed and replaced with 500 µl 70% ethanol.
10. This was centrifuged at 13000 rpm for a further 5 minutes, the supernatant removed, air dried in 37° C. heat block for 2 minutes. DNA was resuspended in 50 µl water.
6. Mutagenesis Reaction
Reagents:
TM buffer (10×): 500 mM Tris-HCl, 100 mM $MgCl_2$, pH7.5
10 mM ATP: (1M stock made by dissolving 0.6052 g in 1 ml water and adjusting pH to 7.0 with 0.1M NaOH. Stock diluted 1:100 to make 10 mM ATP—can be and stored at −70° C.)
100 mM DTT: (1M stock made by dissolving 0.1542 g in 1 ml 0.01M sodium acetate (pH5.2). Stock diluted 1:10 to make 100 mM DTT—can be stored at −20° C.).
Enzymes: T4 polynucleotide kinase, T4 DNA ligase and T7 DNA polymerase from New England Biolabs (NEB).
25 mM dNTPs
Qiagen Qiaquick PCR purification kit (Qiagen)
Phosphorylation of Mutagenic Primer The following were added to an Eppendorf:

| | |
|---|---|
| ssDNA mutagenic primer | 1.0 µg (1.0 µg/132000 daltons = 7.6 pmoles) |
| TM buffer (10×) | 5.5 µl |
| 10 mM ATP | 5 µl |
| 100 mM DTT | 2.5 µl |

Water was added to a total volume of 53 µl. 2 µl (20 U) of T4 polynucleotide kinase (10 U/µl) were added and incubated for 1 hour at 37° C.
Annealing of Mutagenic Primer to Template at a Ratio of 3:1

The following were added to an eppendorf:
dU-ssDNA template (from Section 4) 4.4 µg (4.4 µg/1,750,000 daltons=2.5 pmoles)
phosphorylated mutagenic primer 1.0 µg (1.0 µg/132000 daltons=7.6 pmoles)
TM buffer (10×) 25 µl Water was added to a volume of 250 µl.

The 250 µl was incubated at 90° C. for 2 mins, 50° C. for 3 mins and 20° C. for 5 mins to anneal the mutagenic primer to the template.
Mutagenesis Reaction To the annealed oligo/template mix, the following were added:

| | |
|---|---|
| 10 mM ATP | 10 µl |
| 25 mM dNTP's | 10 µl |
| 100 mM DTT | 15 µl |
| 30 Weiss units T4 DNA ligase (6 U/ul)* | 5 µl |
| 30 units T7 DNA polymerase (10 U/ul) | 3 µl |

*The units marked on the enzyme tube are not Weiss units - 6 U/ul is the correct concentration of enzyme activity The reactions were incubated at 20° C. for 3 hours.

Each reaction was affinity purified to 35 µl water using the Qiagen Qiaquick PCR purification kit. 1 µl of each reaction was run on a 1% agarose gel and compared with the output for the reactions with and without mutagenic primers. An intense ssDNA band (2.5 kb for pCantab6) was observed in the 'without primer' lane. In the 'with primer' lane this ssDNA band was reduced in intensity and replaced by one or more larger bands representing cccDNA (covalently closed circular DNA)(>3 kb for pCantab6).

7. Electroporation into *E. coli* TG1's

Fresh electrocompetent TG1 cells (Stratagene) were prepared according to the following protocol:

1. An appropriate volume of 2TY media was inoculated with a colony from a TG1 minimal media plate. Cells were grown overnight at 25° C. and 300 rpm.
2. 5 flasks containing 500 ml each of 2TY were inoculated with 10 ml (per flask) of the overnight culture. This was grown at 25° C. 300-350 rpm until $OD_{600}$~0.5-0.6) [this usually takes around 2-3 hours]
3. 6×500 ml centrifuge bottles and the Sorval SLA 3000 rotor were pre-chilled to 2° C.
4. Once optimum OD is reached, cells were chilled for 30 mins on ice in the centrifuge bottles and spun at 4,000 rpm for 15 mins at 2° C.
5. The supernatant was poured off and the pellet resuspended in a small volume of ice cold autoclaved MilliQ water. This was made up to ~300 ml with water and spun at 4,000 rpm for 15 mins at 2° C.
6. The supernatant was poured off and resuspended in small volume of the remaining water and then 300 ml water added and spun as above.
7. 8×50 ml Falcon tubes were prechilled at −20° C. A Sorvall bench top centrifuge was prechilled to 2° C.
8. The supernatant was poured off and the pellet resuspended in the remaining water.
9. Once resuspended, this was tipped into the Falcon tubes and water added to 50 ml. This was spun at 3,200 rpms for 10 mins.
10. The supernatant was removed and each pellet was resuspended in a small amount of water, the cells were combined into one 50 ml Falcon tube, made up to 50 ml with water and spun as above.
11. The supernatant was removed and the cells resuspended in remaining volume of water.

For the electroporation a dilution series of cells (cells only) was used to determine a suitable concentration (e.g., dilutions of cells at 100%, 80%, 60% and 50%). The cells only control is plated out on 2TYAG as confirmation that there are no ampicillin-resistant cells in the competent cell preparation.

The total 35 μl completed mutagenesis reaction was electroporated directly into 400 μl electrocompetent TG1 cells in a single cuvette (Bio-Rad *E. coli* Pulser cuvette 0.2 cm electrode gap; Cat No 165-2086), using the following settings:
2.5 kV field strength
200Ω resistance
25 uF capacitance
Time constant ~4.2 milliseconds Immediately after electroporating, 1 ml of 2TYG was added to the cuvette and the cells were transferred to a 50 ml Falcon tube. The cuvette was rinsed with a further 1 ml of 2TYG to transfer the cells from the bottom of the cuvette (with an elongated P200 pipette tip) to the Falcon tube. This was transferred to an incubator at 37° C. and ~150-250 rpm to allow the cells to recover for 1 hour.

A dilution series of each library (each Falcon tube) was plated onto small 2×TYAG plates to estimate library size and the remaining cells on a large 2×TYAG plate. The remaining cells were spun (3200 rpm 10 mins) and resuspended in 1 ml 2TYG before plating on the large plate. The plates were incubated overnight at 30° C.

The library was then scraped from the large plate into 5 ml 2×TY and then supplemented with 2.5 ml 50% glycerol. The cell density was calculated by testing the $OD^{600}$ ($OD^{600}$ of 1=5×10$^8$ cells/ml) of a 1:100 dilution. For storage, multiple aliquots of each library were stored at −70° C., each aliquot containing a ten-fold excess of cells over library size. A single aliquot can then be thawed and added to a 500 ml culture for rescue of the library as phage, e.g, for selection of phage by affinity binding (Hawkins et al (1992) *J. Mol. Biol*, 226, pp 889-896).

The results of this method are as follows, and are also shown in FIG. 4:

|  | Total transformants | No. of sequences analysed | % Mutagenesis efficiency | Mutant library size |
|---|---|---|---|---|
| Recombination library 1 | 1 × 10$^{10}$ | 47 | 83% (39/47) | 8.3 × 10$^9$ |
| Recombination library 2 | 3.9 × 10$^9$ | 43 | 91% (39/43) | 3.5 × 10$^9$ |

Example 2

Subcloning of Ribosome Display Outputs

This example relates to the sub-cloning of outputs from ribosome display. In this subcloning method, the template was a scFv, described as the parent scFv. The protocols used are as for Example 1.

The initial PCR step that produces the mutagenic primer by using the initial primers is carried out on the outputs of a ribosome display library (i.e., RT-PCR products), see Jermutus et al (2001) *PNAS*, vol 98, no 1, 75-80. The oligonucleotides used as the initial PCR primers are shown in FIG. 3.

Thus a repertoire of different scFv sequences from ribosome display outputs (Jermutus et al P.N.A.S 2001, Volume 98 pp 75 to 80) were PCR amplified using a biotinylated forward primer annealing at the beginning of the $V_H$ and the reverse primer mycRestore which primes in the myc tag, just downstream of the end of the $V_L$ (see FIG. 3).

Depending of the amino acid sequence at the beginning of the heavy chain, either Bio-EVQ or Bio-QVQ were used. Standard PCR conditions were used (see Example 1 for details).

The resultant PCR products were separated into single-stranded form to form the mutagenic primers as described in Example 1 and used in the mutagenesis reaction.

The parent molecule for the mutagenesis reaction was single-stranded scFv in pCantab6 (Vaughan et al., (1996) *Nature Biotechnology*, Volume 14 pp 309 to 314). In this example, only a single sequence scFv parent pCantab 6 was used. Thus, the single parent molecule is mutagenised by multiple mutagenic primers thereby to sub-clone the multiple outputs from the ribosome display into the parent plasmid.

The preparation of the single-stranded parent molecule, the protocols for the mutagenesis reaction and for transformation of cells are as for Example 1.

The outputs of the mutagenesis reactions resulted in >10000 transformants after electroporation. In contrast, the control with no mutagenic primer and no enzyme produced ~10 transformants.

The results of the above example were as follows:

| Primer | Size of mutagenic primer | 5' End Complementarity | Mismatch | 3' End Complementarity | Efficiency | n |
|---|---|---|---|---|---|---|
| 2a | 830 bases | 320 bases | 20 bases | 490 bases | 75% | 20 |
| 2b | 830 bases | 700 bases | 20 bases | 110 bases | 90% | 21 |

The mutagenic primers referred to above are shown in the Figures. By comparison, when synthetic oligonucleotides are used in mutagenesis (typically, 18 complementary bases either side of an 18 base mismatch) the average mutagenesis efficiency is 64% (n=350 sequences).

Example 3

Size Exclusion Procedure

Mutagenesis efficiency was further improved by carrying out a size exclusion step on the single-stranded parent molecule of Example 2, prior to the mutagenesis reaction. This resulted in a 1.5× improvement in mutagenesis efficiency (measured by sequence analysis, counting the number of successfully mutated sequences).

The invention claimed is:

1. A method of introducing one or more mutations into a nucleic acid molecule, comprising the following steps:

(a) synthesizing a mutagenic primer from a template nucleic acid molecule by a polymerase chain reaction (PCR)-based method, wherein said mutagenic primer contains one or more mutations relative to a parent molecule;

(b) isolating a single-stranded form of said mutagenic primer from its complementary strand by use of a separating medium;

(c) annealing said single-stranded mutagenic primer to an isolated single-stranded form of said parent molecule; and (d) synthesizing a complementary strand from said mutagenic primer by a non-amplification type reaction, so as to produce a circular-form nucleic acid molecule containing said mutations.

2. The method according to claim 1, wherein prior to said annealing step (c), the single-stranded primer is admixed with the single-stranded parent molecule.

3. The method according to claim 1, further comprising a size exclusion step performed on said isolated single-stranded parent molecule prior to step (c).

4. The method according to claim 1, wherein said isolated single-stranded parent molecule is single-stranded circular DNA.

5. The method according to claim 1, wherein the parent molecule is an expression vector or phage display vector.

6. The method according to claim 1, wherein said circular-form molecule is covalently closed circular DNA.

7. The method according to claim 1, further comprising the step of transforming the mutagenized nucleic acid molecule into host cells.

8. The method according to claim 7, wherein the said transforming is performed using electroporation.

9. The method according to claim 1, comprising a step carried out under conditions such that the complementary strand containing the mutations is preferentially selected.

10. The method of claim 9, wherein said preferential selection of the complementary strand results from the preferential digestion of the parent molecule.

11. The method of claim 9, wherein the parent molecule contains modifications such that the complementary strand is preferentially selected.

12. The method of claim 11, further comprising the step of introducing said modifications.

13. The method of claim 11, wherein the modification is the introduction of dU in place of dT.

14. The method of claim 11, wherein in modification is methylation or the introduction of a conditionally lethal gene.

15. The method of claim 9 wherein said preferential selection is carried out by transforming said circular-form molecule from step (d) into a host cell that is selective for the complementary, non-modified, strand.

16. The method according to claim 1, wherein said PCR-based method is a method in which errors are introduced when synthesising a second strand from a first strand.

17. The method according to claim 16, wherein said method is error-prone PCR.

18. The method according to claim 16, wherein the sequence of the template for the mutagenic primer synthesis is the same as that found in the parent molecule.

19. The method according to claim 1, wherein the step of synthesizing said mutagenic primer introduces a binding moiety in either the positive strand or negative strand of the mutagenic primer and said separation is carried out via said binding moiety binding to its binding partner on said separating medium.

20. The method according to claim 19, wherein said binding moiety is introduced into the positive strand of the mutagenic primer and the negative strand of the mutagenic primer is eluted from said separating medium.

21. The method according to claim 19, wherein said binding moiety is biotin and said binding partner is streptavidin.

22. The method according to claim 1, wherein said mutation(s) include substitutions.

23. The method according to claim 1, wherein said mutation(s) include deletions.

24. The method according to claim 1, wherein said mutation(s) include additions.

25. The method according to claim 1, wherein said mutations are mutations in a plurality of nucleotides.

26. The method according to claim 1, wherein said mutagenic primer has at least 80% complementarity with the parent molecule.

27. The method according to claim 26, wherein said mutagenic primer has at least 90% complementarity with the parent molecule.

28. The method according to claim 27, wherein said mutagenic primer has at least 95% complementarity with the parent molecule.

29. The method according to claim 1, wherein said mutagenic primer is from 100 nucleotides to 4000 nucleotides in size.

30. The method according to claim 1, wherein the molar ratio of mutagenic primer to parent molecule in step (c) is around 3:1.

31. The method according to claim 1, wherein there are multiple parent molecules and/or multiple mutagenic primer molecules.

32. The method according to claim 1, wherein the parent molecule, template or mutagenic primer comprises nucleic acid encoding an antibody variable domain.

33. The method according to claim 32, wherein said antibody variable domain is an antibody VL domain.

34. The method according to claim 32 wherein said antibody variable domain is an antibody VH domain.

35. The method according to claim 32, wherein the parent molecule contains an antibody VH domain and an antibody VL domain and the mutagenic primer molecule contains an antibody VL domain to mutate the VL domain of the parent molecule.

36. The method of claim 32, wherein the parent molecule contains an antibody VL domain and an antibody VH domain and the mutagenic primer molecule contains an antibody VH domain to mutate the antibody VH domain on the parent molecule.

37. The method of claim 35, wherein first and second mutagenic primers are used to mutate the parent molecule, the first mutagenic primer containing an antibody VH domain to mutate the VH domain on the parent molecule and the second mutagenic primer containing an antibody VL domain to mutate the VL domain on the parent molecule.

38. The method of claim 37, wherein said first and second mutagenic primers are used in separate mutagenesis reactions steps.

39. The method of claim 38, wherein said first and second mutagenic primers are used in the same mutagenesis reaction step.

40. The method of claim 35, wherein a single mutagenic primer containing both the VH and the VL domains is used to mutate the VH and the VL domains on the parent molecule.

41. The method according to claim 31, wherein the parent molecule comprises nucleic acid encoding an scFv.

* * * * *

UNITED STATES PATENT AND TRADEMARK OFFICE
CERTIFICATE OF CORRECTION

| | | |
|---|---|---|
| PATENT NO. | : 8,518,645 B2 | Page 1 of 1 |
| APPLICATION NO. | : 11/813507 | |
| DATED | : August 27, 2013 | |
| INVENTOR(S) | : Minter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 813 days.

Signed and Sealed this
Twenty-first Day of April, 2015

Michelle K. Lee
*Director of the United States Patent and Trademark Office*

```
                        SEQUENCE LISTING

<160> NUMBER OF SEQ ID NOS: 15

<210> SEQ ID NO 1
<211> LENGTH: 15
<212> TYPE: PRT
<213> ORGANISM: Artificial
<220> FEATURE:
<223> OTHER INFORMATION: synthetic construct

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 19
<212> TYPE: DNA
<213> ORGANISM: Artificial
<220> FEATURE:
<223> OTHER INFORMATION: synthetic construct

<400> SEQUENCE: 2
gcggcccagc cggccatgg                                                    19

<210> SEQ ID NO 3
<211> LENGTH: 21
<212> TYPE: DNA
<213> ORGANISM: Artificial
<220> FEATURE:
<223> OTHER INFORMATION: synthetic construct

<400> SEQUENCE: 3
accgccagag ccacctccgc c                                                 21

<210> SEQ ID NO 4
<211> LENGTH: 49
<212> TYPE: DNA
<213> ORGANISM: Artificial
```

```
<220> FEATURE:
<223> OTHER INFORMATION: synthetic construct

<400> SEQUENCE: 4
tgttcctttc tatgcggccc agccggccat ggcccaggtc cagctgcag         49

<210> SEQ ID NO 5
<211> LENGTH: 16
<212> TYPE: PRT
<213> ORGANISM: Artificial
<220> FEATURE:
<223> OTHER INFORMATION: synthetic construct

<400> SEQUENCE: 5

Val Pro Phe Tyr Ala Ala Gln Pro Ala Met Ala Gln Val Gln Leu Gln
1               5                   10                  15

<210> SEQ ID NO 6
<211> LENGTH: 54
<212> TYPE: DNA
<213> ORGANISM: Artificial
<220> FEATURE:
<223> OTHER INFORMATION: synthetic construct

<400> SEQUENCE: 6
gtctcgagtg gaggcggcgg ttcaggcgga ggtggctctg gcggtggcgg aagt         54

<210> SEQ ID NO 7
<211> LENGTH: 18
<212> TYPE: PRT
<213> ORGANISM: Artificial
<220> FEATURE:
<223> OTHER INFORMATION: synthetic construct

<400> SEQUENCE: 7

Val Ser Ser Gly Gly Gly Gly Ser Gly Gly Gly Gly Ser Gly Gly Gly
1               5                   10                  15

Gly Ser

<210> SEQ ID NO 8
<211> LENGTH: 49
<212> TYPE: DNA
<213> ORGANISM: Artificial
<220> FEATURE:
<223> OTHER INFORMATION: synthetic construct

<400> SEQUENCE: 8
tgttcctttc tatgcggccc agccggccat ggcccaggtc caactgcag         49

<210> SEQ ID NO 9
<211> LENGTH: 14
<212> TYPE: DNA
<213> ORGANISM: Artificial
<220> FEATURE:
<223> OTHER INFORMATION: synthetic construct

<400> SEQUENCE: 9
ggccgaggtg cagc         14

<210> SEQ ID NO 10
<211> LENGTH: 14
<212> TYPE: DNA
<213> ORGANISM: Artificial
<220> FEATURE:
<223> OTHER INFORMATION: synthetic construct

<400> SEQUENCE: 10
```

```
ggcccaggtg cagc                                                         14

<210> SEQ ID NO 11
<211> LENGTH: 31
<212> TYPE: DNA
<213> ORGANISM: Artificial
<220> FEATURE:
<223> OTHER INFORMATION: synthetic construct

<400> SEQUENCE: 11
gcggcccagc cggccatggc cgaggtgcag c                                      31

<210> SEQ ID NO 12
<211> LENGTH: 31
<212> TYPE: DNA
<213> ORGANISM: Artificial
<220> FEATURE:
<223> OTHER INFORMATION: synthetic construct

<400> SEQUENCE: 12
gcggcccagc cggccatggc ccaggtgcag c                                      31

<210> SEQ ID NO 13
<211> LENGTH: 33
<212> TYPE: DNA
<213> ORGANISM: Artificial
<220> FEATURE:
<223> OTHER INFORMATION: synthetic construct

<400> SEQUENCE: 13
gaacaaaaac tcatctcaga agaggatctg aat                                    33

<210> SEQ ID NO 14
<211> LENGTH: 11
<212> TYPE: PRT
<213> ORGANISM: Artificial
<220> FEATURE:
<223> OTHER INFORMATION: synthetic construct

<400> SEQUENCE: 14

Glu Gln Lys Leu Ile Ser Glu Glu Asp Leu Asn
1               5                   10

<210> SEQ ID NO 15
<211> LENGTH: 24
<212> TYPE: DNA
<213> ORGANISM: Artificial
<220> FEATURE:
<223> OTHER INFORMATION: synthetic construct

<400> SEQUENCE: 15
attcagatcc tcttctgaga tgag                                              24
```